United States Patent
Oda

(10) Patent No.: US 10,417,545 B2
(45) Date of Patent: Sep. 17, 2019

(54) DETECTION DEVICE AND METHOD OF USING THEREOF

(71) Applicant: LAPIS Semiconductor Co., Ltd., Yokohama (JP)

(72) Inventor: Daisuke Oda, Yokohama (JP)

(73) Assignee: LAPIS Semiconductor Co., Ltd., Yokohama (JP)

(*) Notice: Subject to any disclaimer, the term of this patent is extended or adjusted under 35 U.S.C. 154(b) by 0 days.

(21) Appl. No.: 15/879,580

(22) Filed: Jan. 25, 2018

(65) Prior Publication Data

US 2018/0218249 A1    Aug. 2, 2018

(30) Foreign Application Priority Data

Jan. 31, 2017   (JP) ................. 2017-016134

(51) Int. Cl.
| | | |
|---|---|---|
| *G06K 19/07* | (2006.01) | |
| *G08B 21/20* | (2006.01) | |
| *H01Q 1/22* | (2006.01) | |
| *G06K 19/077* | (2006.01) | |
| *H01Q 9/42* | (2006.01) | |

(52) U.S. Cl.
CPC ..... *G06K 19/0717* (2013.01); *G06K 19/0715* (2013.01); *G06K 19/0725* (2013.01); *G06K 19/0775* (2013.01); *G08B 21/20* (2013.01); *H01Q 1/2225* (2013.01); *G01N 2291/02845* (2013.01); *H01Q 9/42* (2013.01)

(58) Field of Classification Search
CPC ........... G06K 19/0717; G06K 19/0775; G06K 19/0715; G06K 19/0725; H01Q 1/2225; H01Q 9/42; G08B 21/20; G01N 2291/02845

USPC ........................... 340/572.1, 612, 618, 572.7
See application file for complete search history.

(56) References Cited

U.S. PATENT DOCUMENTS

| | | | |
|---|---|---|---|
| 9,449,265 B1* | 9/2016 | Maguire | G06K 19/07767 |
| 2006/0132351 A1* | 6/2006 | Le Sesne | G01F 23/284 |
| | | | 342/124 |
| 2007/0101809 A1* | 5/2007 | Roesner | G01F 23/2845 |
| | | | 73/290 R |

FOREIGN PATENT DOCUMENTS

JP          2016-051438 A          4/2016

\* cited by examiner

*Primary Examiner* — Brian Wilson
(74) *Attorney, Agent, or Firm* — Rabin & Berdo, P.C.

(57) ABSTRACT

A detection device includes a first antenna configured to receive a first radio wave transmitted from an external device, a second antenna configured to receive the first radio wave transmitted from the external device, and transmit a second radio wave to the external device; and a chip configured to obtain a comparison result between a first electromotive force generated by the first radio wave received by the first antenna and a second electromotive force generated by the first radio wave received by the second antenna, and to send the comparison result to the external device through the second radio waive. When the first antenna is disposed closer than the second antenna to a place where the existence of moisture is to be detected, a change of the first electromotive force is greater than a change of the second electromotive force in response to the existence of moisture.

7 Claims, 18 Drawing Sheets

DETECTION DEVICE AND METHOD OF USING THEREOF

BACKGROUND OF THE INVENTION

Technical Field

The present invention relates to a detection device.

Background Arts

A detection device using a wireless sensor device is known as a conventional example of a detection device for detecting moisture. Generally, a wireless sensor device includes an IC (integrated circuit) chip having the wireless function, a sensor device, and a power supply mechanism. This wireless sensor device needs to have a power source to supply an operating current for the IC chip and the sensor as well as a driving current for data transfer between the respective chips, and therefore, it is difficult to reduce the price thereof and in some cases, it is also difficult to reduce the size thereof. Examples of power supply mechanisms include a power source such as a battery and a mechanism using the energy harvesting technology such as a solar cell, but both of them are expensive and have specific problems. For example, batteries require maintenance such as replacement and recharging. Also, a mechanism that performs energy harvesting needs to be used in an appropriate environment in order to achieve sufficient performance, and therefore, stable operation performance is not always ensured.

To solve those problems, a detection device using an RFID (radio frequency identifier) tag as a sensor is known (see Japanese Patent Application Laid-open Publication No. 2016-51438, for example). The RFID tag uses the UHF (ultra high frequency) band. In the detection device using the RFID tag as a sensor, moisture is detected based on the attenuation of a radio wave (response signal) received by the communication antenna of the RFID tag, utilizing a communication degradation property according to which the response signal attenuation occurs when the radio wave transmitted by the reader/writer passes through moisture.

SUMMARY OF THE INVENTION

However, in the detection device using the RFID tag as a sensor, the presence or absence of moisture is detected based on the attenuation of a radio wave received by the communication antenna. The attenuation of a radio wave caused by moisture adversely affects communications with the reader/writer in some cases.

Generally, the intensity of the radio wave changes depending on the distance between the RFID tag and the reader/writer (communication distance). Thus, it was difficult to determine whether the degradation of the communication property occurred due to the presence of moisture or a prolonged communication distance, which could lower the moisture detection accuracy.

The invention aims to provide a detection device that suppresses the degradation of moisture detection accuracy and the degradation of communication property.

According to an aspect of the invention, there is provided a detection device of the invention includes a first antenna configured to receive a first radio wave transmitted from an external device, a second antenna configured to receive the first radio wave transmitted from the external device, and transmit a second radio wave to the external device; and a chip configured to obtain a comparison result between a first electromotive force generated by the first radio wave received by the first antenna and a second electromotive force generated by the first radio wave received by the second antenna, and to send the comparison result to the external device through the second radio waive, such that when the first antenna is disposed closer than the second antenna to a place where the existence of moisture is to be detected, a change of the first electromotive force is greater than a change of the second electromotive force in response to the existence of moisture.

According to an aspect of the invention, there is provided a method of using a detection device for detecting the existence of moisture. The detection device includes a first antenna configured to receive a first radio wave transmitted from an external device, and a second antenna configured to receive the first radio wave transmitted from the external device, and transmit a second radio wave to the external device, and a chip configured to obtain a comparison result between a first electromotive force generated by the first radio wave received by the first antenna and a second electromotive force generated by the first radio wave received by the second antenna, and to send the comparison result to the external device through the second radio wave. The method includes disposing the first antenna closer than the second antenna to a place where the existence of moisture is to be detected; and in response to a change of the first electromotive force that is varied greater than a change of the second electromotive force, detecting the existence of moisture.

According to the invention, it is possible to achieve improved accuracy of moisture detection and reduced signal degradation resulting from the detected moisture.

DETAILED DESCRIPTION OF THE INVENTION

Below, embodiments of the invention will be explained in detail with reference to the drawings. In each embodiment, an RFID system is used to detect moisture, and the RF tag is used in one example of a detection device configured to detect moisture.

Embodiment 1

Figure 1:
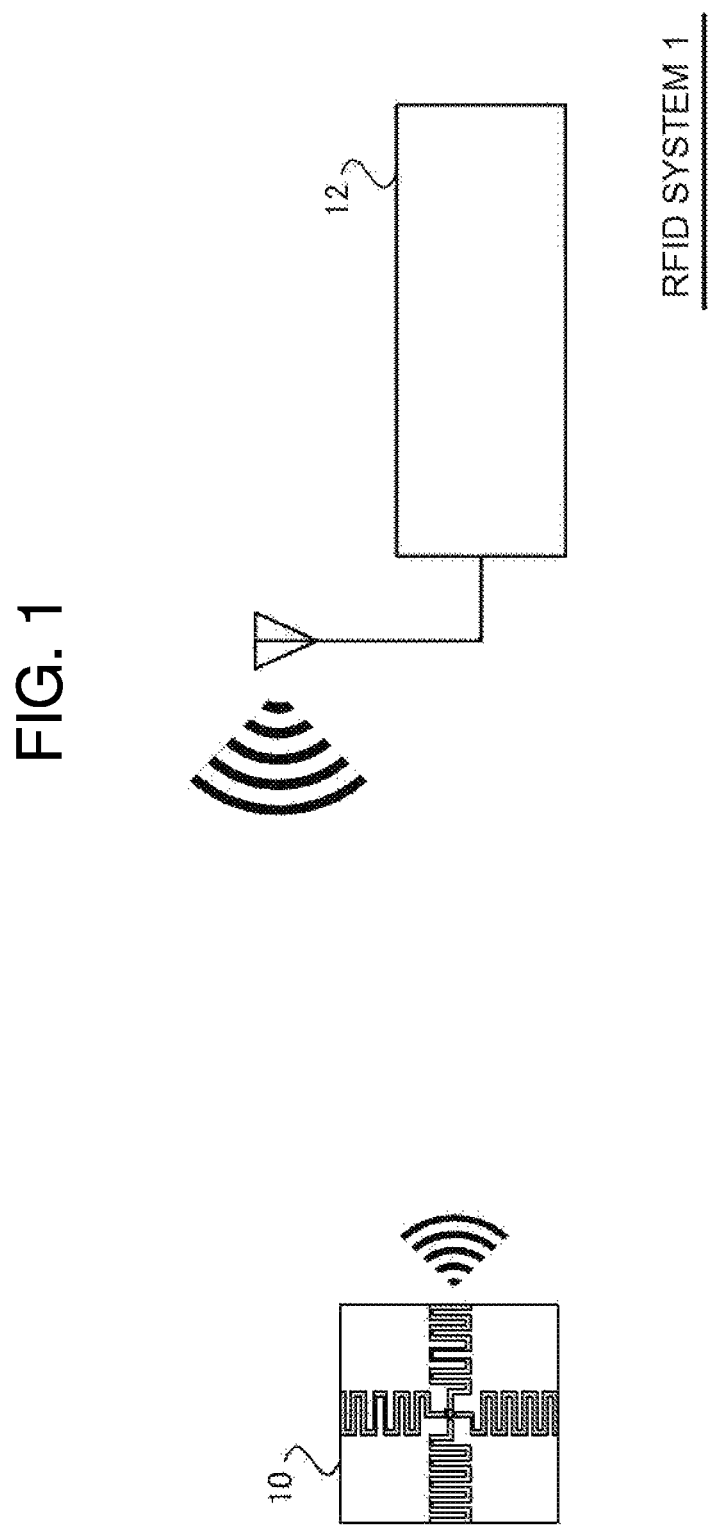
FIG. 1 is a configuration diagram showing a schematic view of an example of a semiconductor storage device of Embodiment 1.

First, the configuration of an RFID system, for moisture detection of this embodiment, will be explained. FIG. 1 shows a schematic configuration diagram showing an example of the RFID system 1 of this embodiment.

As shown in FIG. 1, the RFID system 1 of this embodiment includes an RF tag 10 and a reader/writer 12. The reader/writer 12 of this embodiment has the function of causing the RF tag 10 to detect moisture, the function of reading out the data stored in the RF tag 10, and the function of storing (writing) data in the RF tag 10. The reader/writer 12 of this embodiment corresponds to one example of the external device of the invention.

On the other hand, the RF tag 10 of this embodiment is a radio-wave RF tag, and has the functions of: (1) detecting moisture and outputting a detection result to the reader/writer 12, (2) reading stored data and outputting the data to the reader/writer 12, and (3) storing the data received from the reader/writer 12.

Figure 2:
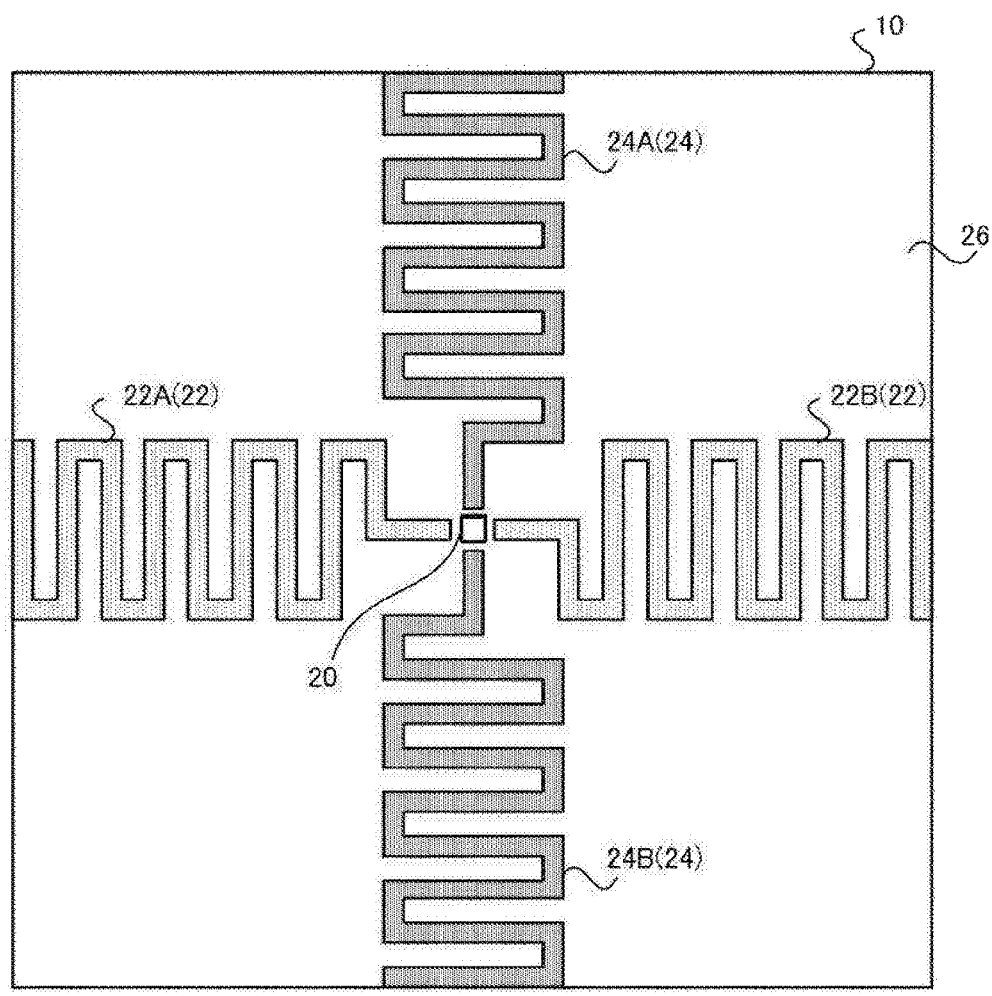
FIG. 2 is a plan view showing a schematic configuration of one example of an RF tag of Embodiment 1.

FIG. 2 is a plan view showing a schematic configuration of one example of the RF tag 10 of Embodiment 1. As shown in FIG. 2, the RF tag 10 of this embodiment includes an IC chip 20, a second antenna (hereinafter referred to as a communication antenna) 22 (22A, 22B), and a first antenna (hereinafter referred to as a moisture detection antenna) 24 (24A, 24B). The IC chip 20, the communication antenna 22, and the moisture detection antenna 24 are disposed on the surface of a base 26.

The communication antenna 22 has the function of receiving a radio wave transmitted from the reader/writer 12 and the function of transmitting read-out data or moisture detection result to the reader/writer 12 via a radio wave. As shown in FIG. 2, the communication antenna 22 of this embodiment includes an antenna element 22A and an antenna element 22B, and the antenna element 22A and the antenna element 22B are disposed facing each other across the IC chip 20. The antenna element 22A and the antenna element 22B of this embodiment are one example of the first communication antenna and the second communication antenna of the invention. Although not shown in FIG. 2, the antenna element 22A and the IC chip 20, and the antenna 22B and the IC chip 20 are electrically connected to each other, respectively (see FIGS. 3 and 4).

The moisture detection antenna 24 has the function of receiving a radio wave transmitted from the reader/writer 12. As shown in FIG. 2, the moisture detection antenna 24 of this embodiment includes an antenna element 24A and an antenna element 24B, and the antenna element 24A and the antenna element 24B are disposed facing each other across the IC chip 20. The antenna element 24A and the antenna element 24B of this embodiment are one example of the first detection antenna and the second detection antenna of the invention. Although not shown in FIG. 2, the antenna element 24A and the IC chip 20, and the antenna element 24B and the IC chip 20 are electrically connected to each other, respectively (see FIGS. 3 and 4).

In this embodiment, the direction in which the wiring of the communication antenna 22 extends is referred to as the "wiring direction" of the communication antenna 22, and specifically, the direction along which the antenna element 22A, the IC chip 20, and the antenna element 22B are arranged is referred to as the "wiring direction" of the communication antenna 22. Similarly, the direction in which the wiring of the moisture detection antenna 24 extends is referred to as the "wiring direction" of the moisture detection antenna 24, and specifically, the direction along which the antenna element 24A, the IC chip 20, and the antenna element 24B are arranged is referred to as the "wiring direction" of the moisture detection antenna 24.

As shown in FIG. 2, in the RF tag 10 of this embodiment, the wiring direction of the moisture detection antenna 24 and the wiring direction of the communication antenna 22 intersect with each other. In other words, the communication antenna 22 and the moisture detection antenna 24 are arranged to cross each other. More specifically, in the RF tag 10 of this embodiment, the wiring direction of the moisture detection antenna 24 and the wiring direction of the communication antenna 22 intersect with each other at the position where the IC chip 20 is located.

As shown in FIG. 2, in the RF tag 10 of this embodiment, the antenna element 22A, the antenna element 22B, the antenna element 24A and the antenna element 24B are formed to have similar shapes. For example, as shown in FIG. 2, the antenna elements 22A, 22B, 24A, and 24B of this embodiment are folded a plurality of times in the wiring direction (having a plurality of folded parts) so that the length in the wiring direction of the area where the wiring is disposed is reduced.

There is no special limitations on the material for the communication antenna 22 and the moisture detection antenna 24, and a material that is generally used for a UHF antenna can be used, for example.

Figure 3:
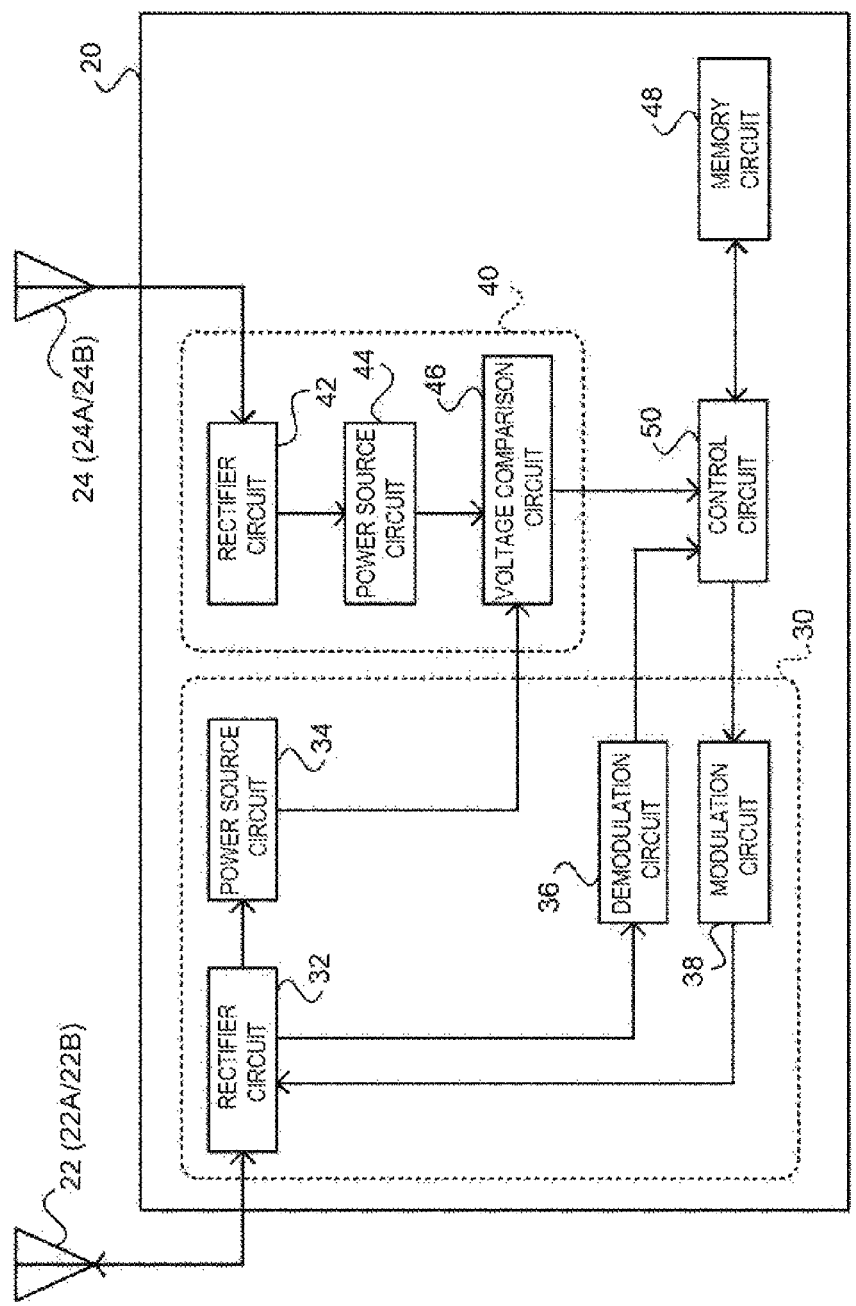
FIG. 3 is a block diagram showing the configuration of one example of an IC chip of Embodiment 1.

As shown in FIG. 3, the IC chip 20 of this embodiment includes an RF control circuit 30, a sensor circuit 40, a memory circuit 48, and a control circuit 50.

The control circuit 50 has the function of controlling the overall operation of the IC chip 20. A CPU (central processing unit) and the like maybe used for the control circuit 50, but there is no special limitation thereon. The control circuit 50 of this embodiment is one example of the controller of the invention.

The memory circuit 48 is a non-volatile storage part, and stores data received from a prescribed ID or the reader/writer 12, for example.

As shown in FIG. 3, the RF control circuit 30 of this embodiment includes a rectifier circuit 32, a power source circuit 34, a demodulation circuit 36, and a modulation circuit 38. On the other hand, as shown in FIG. 3, the sensor circuit 40 of this embodiment includes a rectifier circuit 42, a power source circuit 44, and a voltage comparison circuit 46.

As described above, the sensor circuit 40 of this embodiment differs from the RF control circuit 30 in having the voltage comparison circuit 46, instead of the demodulation circuit 36 and the modulation circuit 38, which are necessary for the data communication with the reader/writer 12.

The RF control circuit 30 of this embodiment has a configuration of a general RF tag to communicate with the reader/writer.

The rectifier circuit 32 of the RF control circuit 30 is connected to the communication antenna 22, and configured to rectify a radio wave of the UHF band received by the communication antenna 22 from the reader/writer 12, and output the radio wave to the power source circuit 34 and the demodulation circuit 36. The demodulation circuit 36 decodes a communication signal included in the radio wave rectified by the rectifier circuit 32, and outputs the decoded signal to the control circuit 50. The modulation circuit 38 encodes (modulates) the signal input from the control circuit 50, and the outputs the encoded signal to the rectifier circuit 32.

The power source circuit 34 converts the electromotive force generated by the radio wave rectified by the rectifier circuit 32 to a DC voltage, and outputs the DC voltage to the voltage comparison circuit 46. The electromotive force generated by a radio wave received through the communication antenna 22 of this embodiment is one example of the second electromotive force of the invention. The power source circuit 34 of this embodiment generates a power source voltage for operating each part of the IC chip 20 from the electromotive force, and supplies the power source voltage to each part.

The rectifier circuit 42 of the sensor circuit 40 is connected to the moisture detection antenna 24, and configured to rectify a radio wave of the UHF band received by the moisture detection antenna 24 from the reader/writer 12, and output the radio wave to the power source circuit 44. The power source circuit 44 outputs the electromotive force generated by the radio wave rectified by the rectifier circuit 42 to the voltage comparison circuit 46. The electromotive force generated by the radio wave received through the moisture detection antenna 24 of this embodiment is one example of the first electromotive force of the invention.

The voltage comparison circuit 46 outputs the information indicating the comparison result between the electromotive force output from the power source circuit 34 and the electromotive force output from the power source circuit 44 to the control circuit 50 as digital data.

Figure 4:
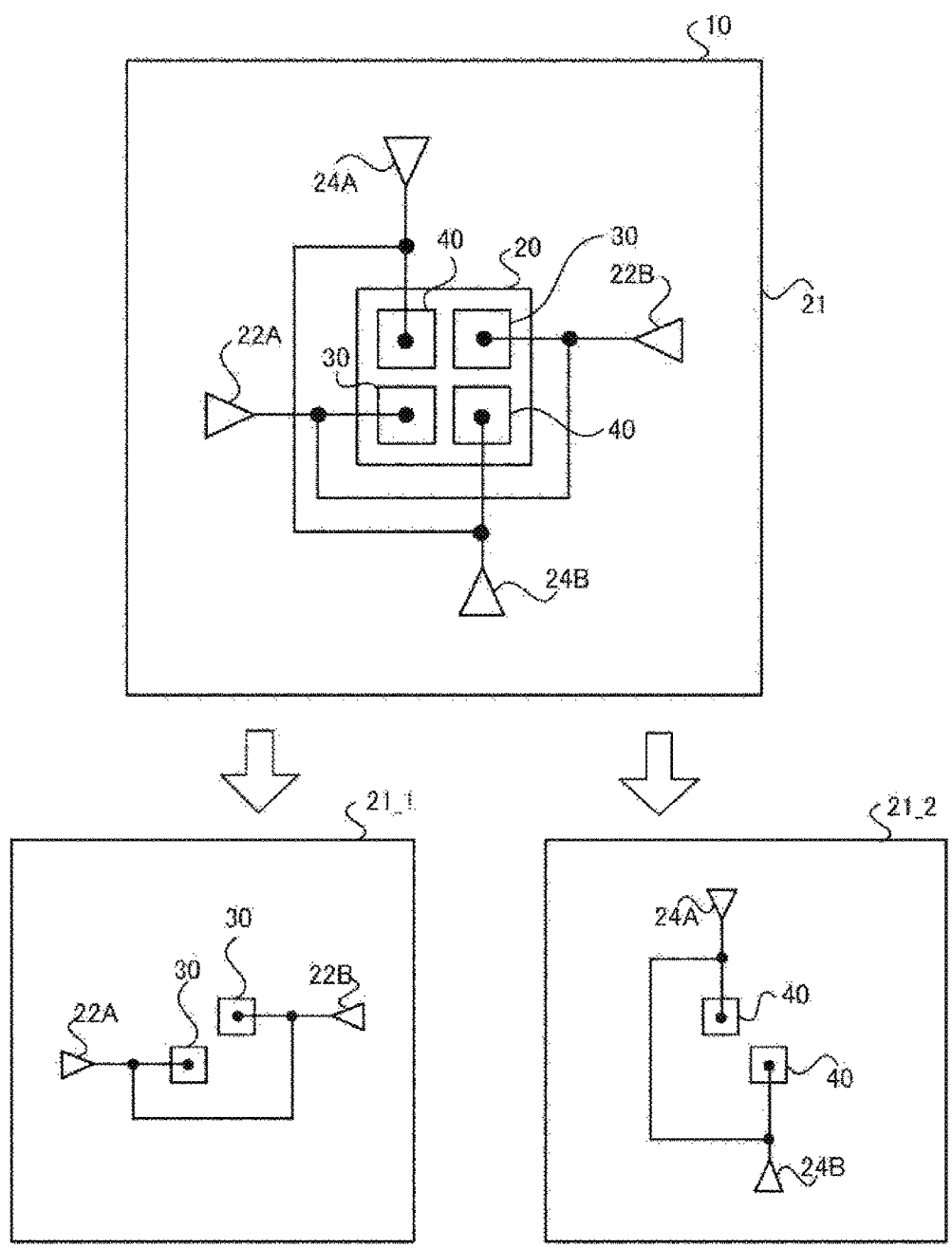
FIG. 4 is a plan view for explaining an example of the inlay structure of the RF tag of Embodiment 1.

As shown in FIG. 4, in the RF tag 10 of this embodiment, an in-lay 21 has the multilayer structure in which a first layer 21_1 and a second layer 21_2 are stacked. An inductance component is present between the antenna element 22A and the antenna element 22B of the communication antenna 22 and between the antenna element 24A and the antenna element 24B of the moisture detection antenna 24, respectively. Thus, if the in-lay has only one layer, the communication antenna 22 and the moisture detection antenna 24 would be short-circuited. In this embodiment, however, as shown in FIG. 4, the first layer 21_1 having the communication antenna 22 arranged therein and connected to the RF control circuit 30, and the second layer 21_2 having the moisture detection antenna 24 arranged therein and connected to the sensor circuit 40 are stacked, thereby preventing the short-circuit.

Next, the operation of the RF tag 10 of this embodiment will be explained. In the RF tag 10 of this embodiment, when the communication antenna 22 receives a radio wave of the UHF band from the reader/writer 12, the received radio wave is converted to a power voltage by the power source circuit 34 via the rectifier circuit 32, and supplied to the respective parts of the IC chip 20. This power voltage activates the IC chip 20. The communication signal included in the radio wave transmitted from the reader/writer 12 includes a signal indicating the instruction information for either reading ID data or the like stored in the memory circuit 48 (ID reading), writing the ID data into the memory circuit 48 (ID writing), or detecting moisture.

Figure 5:
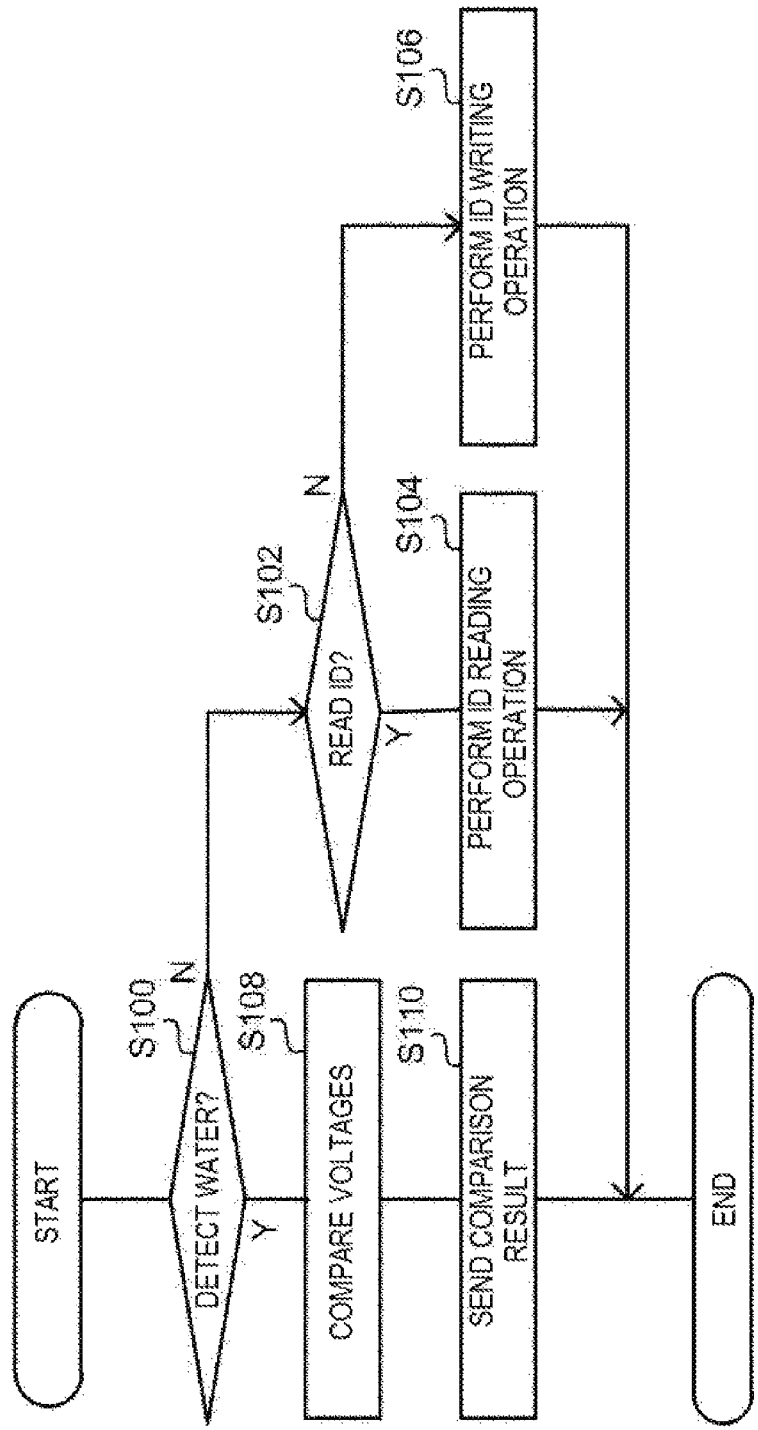
FIG. 5 is a flowchart showing an example of the operation flow of the IC chip of Embodiment 1.

In the activated state, the control circuit 50 performs a series of operations shown in the flowchart of FIG. 5.

In Step S100, the control circuit 50 determines whether or not the instruction information indicates moisture detection, or more specifically, whether or not the signal is calling upon the moisture detection. As described above, the control circuit 50 has a communication signal decoded by the demodulation circuit 36. Thus, the control circuit 50 reads out the instruction signal included in the communication signal. If the instruction information in the communication signal is either ID reading or ID writing, the determination result in Step S100 is No, and thus, the process moves to Step S102.

In Step S102, the control circuit 50 determines whether the instruction information in the communication signal is ID reading or not. If the instruction information in the communication signal is ID reading, the determination result of Step S102 is Yes, and thus, the process moves to Step S104.

In Step S104, the control circuit 50 performs the ID reading operation, and ends the series of operations shown in FIG. 4. The ID reading operation in this step is the same as the ID reading operation of a general RFID tag. That is, the control circuit 50 reads out data indicating IDs stored in the memory circuit 48 (will be referred to as "ID data" below), and outputs the data to the modulation circuit 38. The read-out ID data is modulated by the modulation circuit 38, and sent to the reader/writer 12 from the communication antenna 22 via the rectifier circuit 32. The reader/writer 12 recognizes the ID of the RF tag 10 by receiving the ID data sent from the RF tag 10.

If the instruction information in the communication signal is ID writing, the determination result of Step S102 is No, and thus, the process moves to Step S106. In Step S106, the control circuit 50 performs the ID writing operation, and ends the series of operations shown in FIG. 4. The ID writing operation in this step is the same as the ID writing operation of a general RFID tag. That is, the control circuit 50 recognizes the ID to be written based on the signal decoded by the demodulation circuit 36, and writes the ID in the memory circuit 48. After the data is written, the control circuit 50 outputs, to the modulation circuit 38, a writing completion signal indicating that the data writing has been completed. The writing completion signal is modulated by the modulation circuit 38, and sent to the reader/writer 12 from the communication antenna 22 via the rectifier circuit 32. The reader/writer 12 confirms that the ID has been written into the RF tag 10 by receiving the writing completion signal sent from the RF tag 10.

If the instruction information in the communication signal is moisture detection, the determination result of Step S100 is Yes, and thus, the process moves to Step S108. In Step S108, the control circuit 50 causes the voltage comparison circuit 46 to compare the voltage value output from the power source circuit 34 of the RF control circuit 30 with the voltage value output from the power source circuit 44 of the sensor circuit 40. In the subsequent step S110, the control circuit 50 performs the process to send the comparison result provided by the voltage comparison circuit 46 to the reader/writer 12, and ends the series of operations shown in FIG. 4.

The radio wave transmitted from the reader/writer 12 is also received by the moisture detection antenna 24. The received radio wave is input into the power source circuit 44 via the rectifier circuit 42, converted to a DC voltage by the power source circuit 44, and output to the voltage comparison circuit 46, in a manner similar to the power source circuit 34 of the RF control circuit 30.

In the RF tag 10 of this embodiment, moisture is detected by the voltage comparison circuit 46 comparing the DC voltage provided by the power source circuit 44 with the DC voltage provided by the power source circuit 34. The method to detect moisture in the RF tag 10 of this embodiment will be explained in further detail with reference to FIG. 6.

Figure 6:
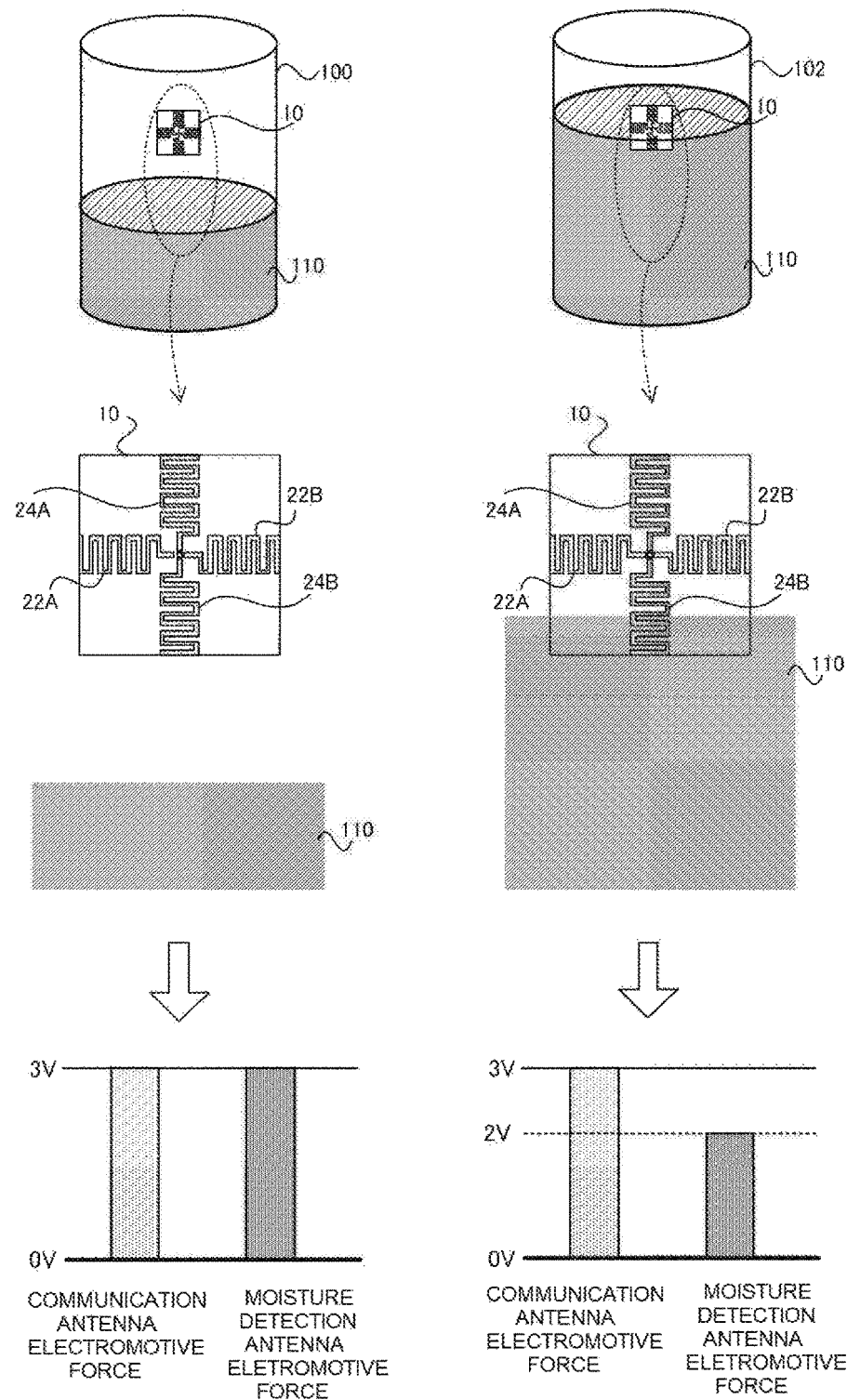
FIG. 6 is a diagram for explaining how to detect moisture by the RF tag of Embodiment 1.

In the example shown in FIG. 6, a RF tag 10 is each pasted on the outer surface of a container 100 and a container 102. The surface level of liquid 110 inside of the container 100 is far from the RF tag 10. In this case, the electromotive force generated in the power source circuit 34 by the radio wave received by the communication antenna 22 (will be referred to as a "communication antenna electromotive force" below) is equal to the electromotive force generated in the power source circuit 44 by the radio wave received by the moisture detection antenna 24 (will be referred to as a "moisture detection antenna electromotive force" below). For example, if the electromotive force generated in the power source circuit 34 by the radio wave received by the communication antenna 22 is 3V, the electromotive force generated in the moisture detection antenna 24 is also 3V as shown in FIG. 6.

On the other hand, the surface level of liquid 110 inside of the container 102 is at the same level as the RF tag 10. In this case, as shown in FIG. 6, the antenna element 24B is in indirect contact with the liquid 110 through the container 102. For ease of explanation, in the descriptions below, "being in contact" includes both cases where the RF tag 10 is in contact with the liquid (moisture) directly and indirectly. Because the antenna element 24B is in contact with the liquid 110, the antenna element 24B receives a radio wave that has been attenuated due to the effect of the liquid 110. Generally, when liquid is present nearby, a radio wave is attenuated. Thus, the radio wave reaching the moisture detection antenna 24 is attenuated as compared with that for the communication antenna 22. As a result, as shown in FIG. 6, the moisture detection antenna electromotive force (2V, for example) is smaller than the communication antenna electromotive force (3V). Also, because the radio wave is attenuated when passing through the liquid 110, the greater the area of the moisture detection antenna 24 touching the liquid 110 is, the smaller the moisture detection antenna electromotive force is relative to the communication antenna electromotive force.

In the RF tag 10 of this embodiment, the voltage comparison circuit 46 outputs to the control circuit 50 the comparison result, which is the information indicating whether the communication antenna electromotive force is equal to the moisture detection antenna electromotive force or not, taking errors into consideration. If the comparison result is the information indicating that the communication antenna electromotive force is equal to the moisture detection antenna electromotive force, the control circuit 50 determines that no moisture is present nearby. If the comparison result is the information indicating that the communication antenna electromotive force is not equal to the moisture detection antenna electromotive force, the control circuit 50 determines that moisture is present nearby.

In Step S108, the control circuit 50 of this embodiment sends information indicating the presence or absence of moisture obtained from the comparison result to the reader/writer 12, instead of sending the comparison result provided by the voltage comparison circuit 46 as is. However, the invention is not limited to this, and the RF tag 10 may be configured to send the comparison result as is to the reader/writer 12, and the reader/writer 12 may be configured to determine the presence or absence of moisture based on the comparison result.

In the RF tag 10 of this embodiment, even when the instruction information included in the communication signal is ID reading or ID writing, instead of moisture detection, the moisture detection antenna 24 receives a radio wave. In this case, the comparison result between the communication antenna electromotive force and the moisture detection antenna electromotive force is provided by the voltage comparison circuit 46 to the control circuit 50. In this embodiment, the control circuit 50 may be configured to receive the input even when the moisture detection is not to be performed.

As described above, the RF tag 10 of this embodiment includes two types of antennas: the communication antenna 22 and the moisture detection antenna 24. This way, the effect of moisture on the communication antenna 22 can be suppressed, which makes it possible to mitigate the degradation of the communication characteristics.

In the RF tag 10 of the embodiment above, the presence or absence of moisture is detected based on the comparison result between the communication antenna electromotive force and the moisture detection antenna electromotive force, and therefore, as compared with the case of using the communication antenna only, the accuracy of moisture detection can be improved.

Embodiment 2

In the RF tag 10 of Embodiment 1, the voltage comparison circuit 46 compares the communication antenna electromotive force with the moisture detection antenna electromotive force. On the other hand, in the RF tag 10 of this embodiment, a value obtained by digitalizing the communication antenna electromotive force is compared with a value obtained by digitalizing the moisture detection antenna electromotive force.

The configuration of the RFID system 1 of this embodiment is the same as that of the RFID system 1 of Embodiment 1 (see FIG. 1). The configuration of the RF tag 10 of this embodiment is the same as that of the RF tag 10 of Embodiment 1 (see FIG. 2). The configuration of the IC chip 20 of this embodiment, however, differs from that of the IC chip 20 of Embodiment 1 (see FIG. 3).

Figure 7:
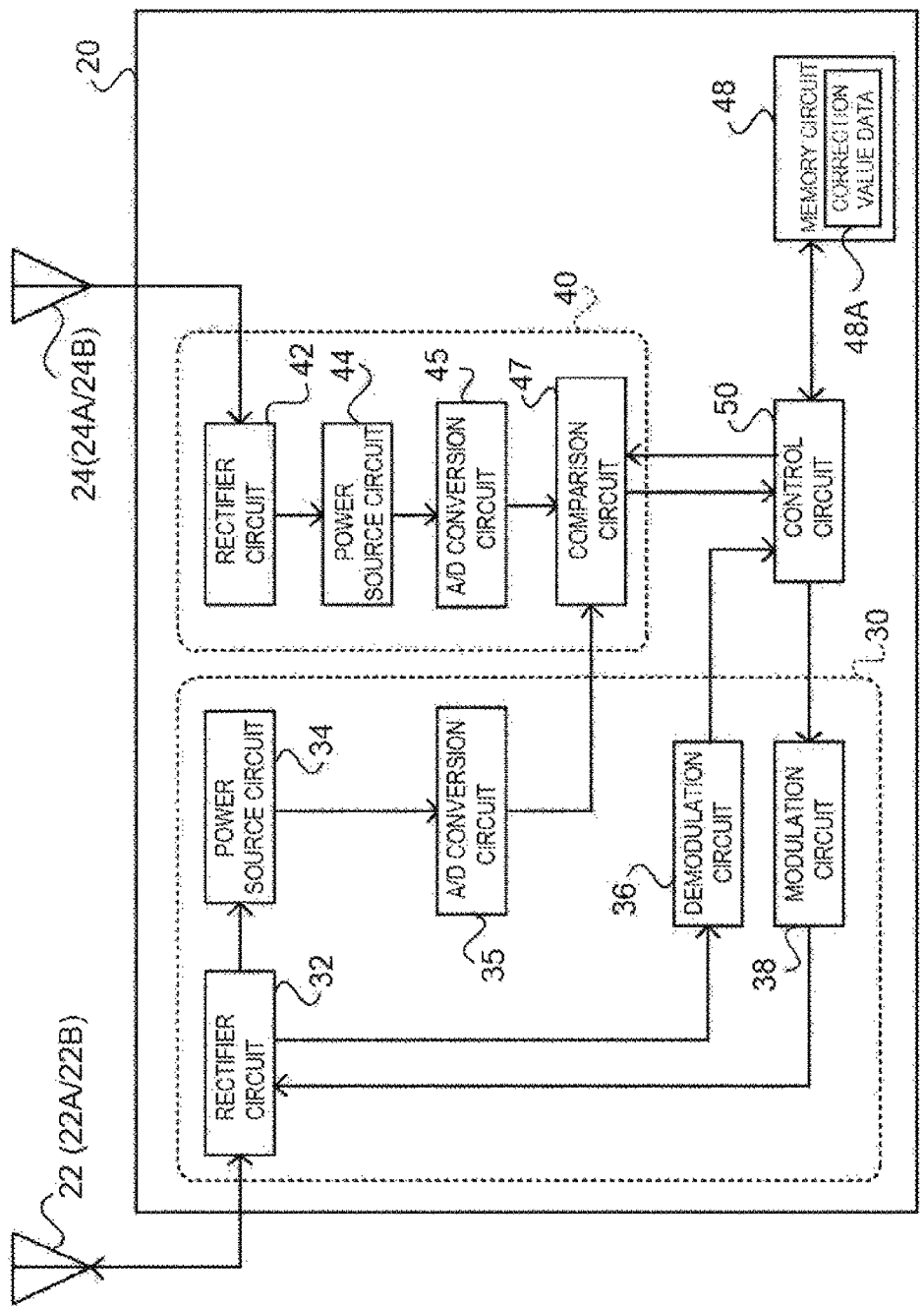
FIG. 7 is a block diagram showing the configuration of one example of an IC chip of Embodiment 2.

FIG. 7 is a block diagram showing the configuration of one example of an IC chip of this embodiment. As shown in FIG. 7, the IC chip 20 of this embodiment differs from the IC chip 20 of Embodiment 1 (see FIG. 3) in that the RF control circuit 30 further includes an A/D (analog/digital) conversion circuit 35. Also, the IC chip 20 of this embodiment differs from the IC chip 20 of Embodiment 1 (see FIG. 3) in that the sensor circuit 40 includes an A/D (analog/digital) conversion circuit 45 and a comparison circuit 47. Furthermore, as shown in FIG. 7, the IC chip 20 of this embodiment differs from the IC chip 20 of Embodiment 1 (see FIG. 3) in that the memory circuit 48 contains correction value data 48A.

The A/D conversion circuit 35 coverts a DC voltage output from the power source circuit 34 to a digital value, and outputs the converted digital value to the comparison circuit 47. The A/D conversion circuit 45 coverts a DC voltage output from the power source circuit 44 to a digital value, and outputs the converted digital value to the comparison circuit 47.

The comparison circuit 47 compares the digital value provided by the A/D conversion circuit 35 with the digital value provided by the A/D conversion circuit 45. That is, the comparison circuit 47 of this embodiment differs from the voltage comparison circuit 46 of Embodiment 1 in comparing the communication antenna electromotive force with the moisture detection antenna electromotive force using numerical values. Furthermore, the comparison circuit 47 of this embodiment corrects the comparison result using the correction value data 48A in the memory circuit 48, and outputs the corrected comparison result to the control circuit 50.

Next, the operation of the IC chip 20 of this embodiment will be explained. The overall flow of the operation is similar to the operation of the IC chip 20 of Embodiment 1 (see FIG. 5), but the moisture detection operation of this embodiment differs from that of Embodiment 1, and therefore, the moisture detection operation in the IC chip 20 of this embodiment will be explained.

In Embodiment 1, when there is no moisture nearby, the communication antenna electromotive force was equal to the moisture detection antenna electromotive force. However, depending on manufacturing variations of the IC chip 20, the communication antenna 22, and the moisture detection antenna 24 or the usage status of the RF tag 10 (such as the surrounding environment or attachment condition), the communication antenna electromotive force may differ from the moisture detection antenna electromotive force.

Figure 8:
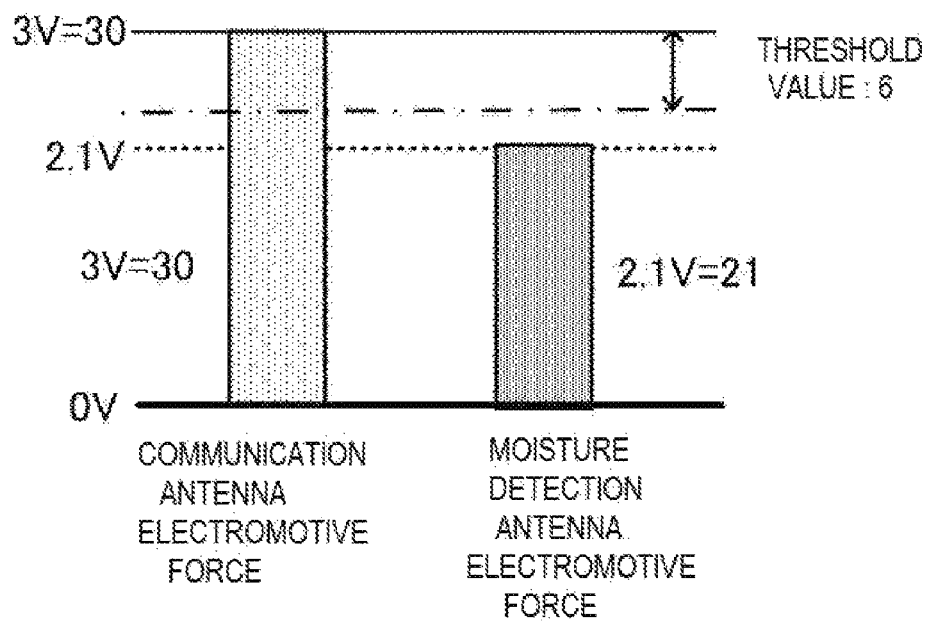
FIG. 8 is a diagram for explaining how to detect moisture by the RF tag of Embodiment 1.

For example, as shown in FIG. 8, even when there is no moisture nearby, there could be a case in which the communication antenna electromotive force is 3V (digital value thereof is 30) and the moisture detection antenna electromotive force is 2.1V (digital value thereof is 20). Below, using this case as a specific example, the principle (operation) of detecting moisture by the IC chip 20 of this embodiment will be explained.

As shown in FIG. 8, the communication antenna electromotive force differs from the moisture detection antenna electromotive force even though there is no moisture nearby, which could cause an erroneous detection of moisture. In order to solve this problem, in the IC chip 20 of this embodiment, a difference between the communication antenna electromotive force and the moisture detection antenna electromotive force is obtained as a correction value in advance, and the obtained correction value is stored in the memory circuit 48 as the correction value data 48A.

Figure 9A:
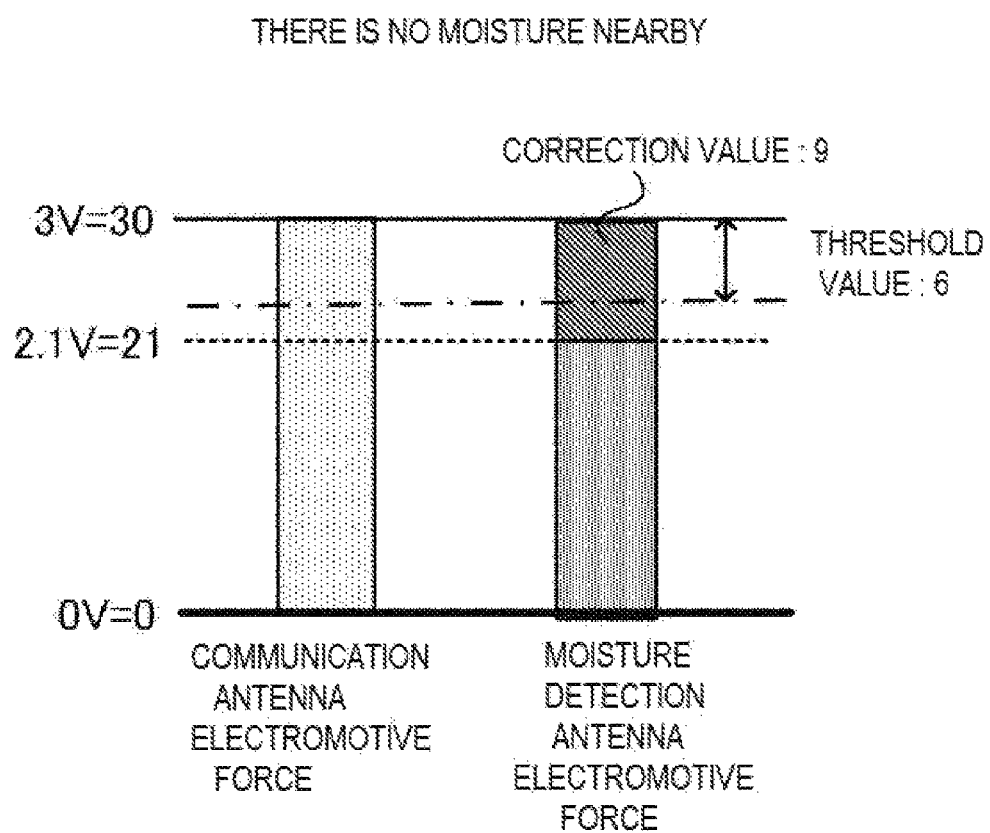
FIG. 9A is a diagram for explaining how to detect moisture by the RF tag of Embodiment 2.

In this specific example, as shown in FIG. 9A, the control circuit 50 obtains the difference between the communication antenna electromotive force "30" and the moisture detection antenna electromotive force "21," which is "9," and stores the value "9" in the memory circuit 48 as the correction data 48A.

There is no special limitation on the method and the like for the control circuit 50 of the IC chip 20 to obtain this correction value. For example, when there is no moisture nearby, the reader/writer 12 may transmit an instruction signal for obtaining the correction value, and when the RF tag 10 receives the instruction signal, the control circuit 50 may find the correction value based on the communication antenna electromotive force and the moisture detection antenna electromotive force.

In this case, a plurality of instruction signals sent from the reader/writer 12 to the RF tag 10 further include an instruction signal for obtaining the correction value and storing the correction value data 48A in the memory circuit 48 (will be referred to as a "correction value obtaining signal"), in addition to the instruction signals of Embodiment 1. The control circuit 50 of the IC chip 20 adds a step of determining whether the received instruction signal is the correction value obtaining signal or not, and if the instruction signal is the correction value obtaining signal, a step of obtaining the correction value and storing the correction value data 48A in the memory circuit 48, to the operation flow shown in FIG. 5. In this case, the correction value obtaining signal (one instruction signal) instructs two operations (obtaining the correction value and writing the correction value data 48A into the memory circuit 48), but the invention is not limited to this, and there may be two separate instruction signals: an instruction signal for obtaining the correction value; and an instruction signal for writing the correction value data 48A into the memory circuit 48.

Alternatively, the correction value data 48A sent from the reader/writer 12 may be sent to the RF tag 10, and the control circuit 50 may store the received correction value data 48A in the memory circuit 48.

In this case, a plurality of instruction signals sent from the reader/writer 12 to the RF tag 10 further include a correction value writing signal for receiving the correction value data 48A sent by the reader/writer 12, and storing the received correction value data 48A in the memory circuit 48, in addition to the instruction signals of Embodiment 1. The control circuit 50 of the IC chip 20 adds a step of determining whether the received instruction signal is a correction value writing signal or not, and if the instruction signal is the correction value writing signal, a step of storing the correction value data 48A received from the reader/writer 12 into the memory circuit 48, to the operation flow shown in FIG. 5.

The IC chip 20 of this embodiment is configured such that the threshold value for moisture detection is determined in advance, the comparison circuit 47 compares the difference between the communication antenna electromotive force and the moisture detection antenna electromotive force, which are corrected by the correction value, with the threshold value, and if the difference is equal to or greater than the threshold value, the control circuit 50 determines that moisture is present nearby. Thus, in the IC chip 20 of this embodiment, the control circuit 50 reads out the correction value data 48A from the memory circuit 48, and outputs the correction value data 48A to the comparison circuit 47.

When there is no moisture nearby, as shown in FIG. 9A, for example, the comparison circuit 47 receives "30" as the communication antenna electromotive force from the A/D conversion circuit 35, and "21" as the moisture detection antenna electromotive force from the A/D conversion circuit 45. The comparison circuit 47 determines whether the difference between the communication antenna electromotive force and the value obtained by adding the correction value "9," which is provided by the control circuit 50, to the moisture detection antenna electromotive force (21+9=30) is equal to or greater than the threshold value "6," and outputs the comparison result to the control circuit 50.

In the state shown in FIG. 9A, the comparison circuit 47 outputs information indicating that the difference is smaller than the threshold value, which is the comparison result, to the control circuit 50. In this case, the control circuit 50 determines that there is no moisture nearby, and sends the comparison result to the reader/writer 12 (See Step S108 in FIG. 5).

Figure 9B:
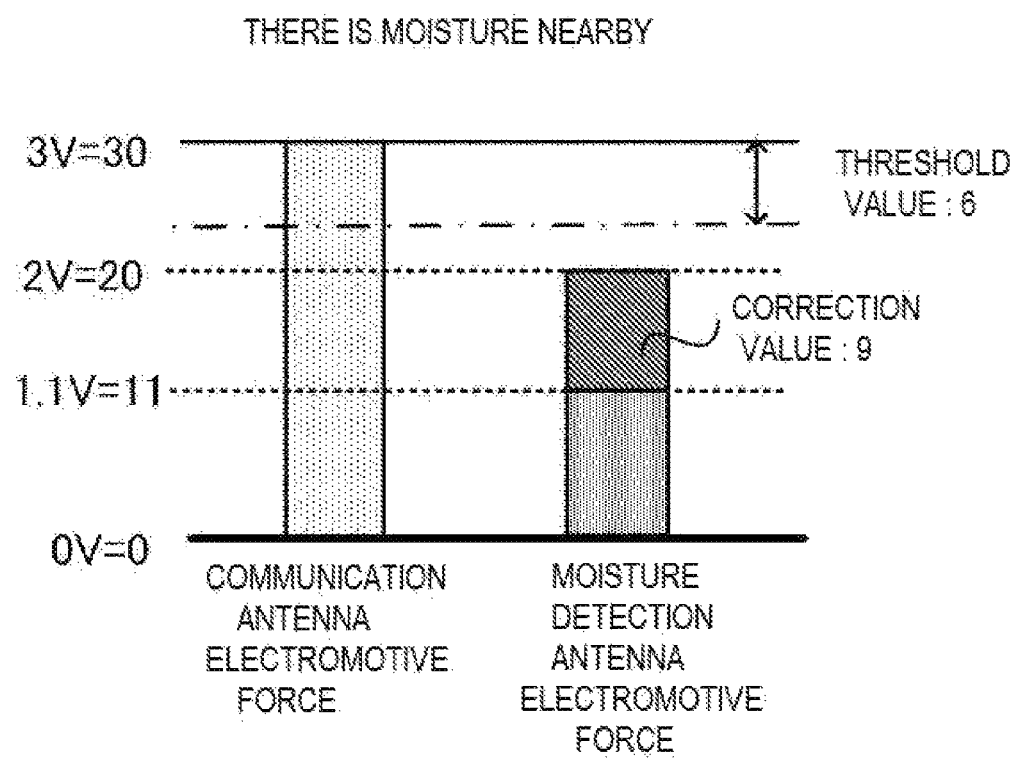
FIG. 9B is a diagram for explaining how to detect moisture by the RF tag of Embodiment 2.

On the other hand, when there is moisture nearby, as shown in FIG. 9B, for example, the comparison circuit 47 receives "30" as the communication antenna electromotive force from the A/D conversion circuit 35, and "11" as the moisture detection antenna electromotive force from the A/D conversion circuit 45. The comparison circuit 47 determines whether the difference between the communication antenna electromotive force and the value obtained by adding the correction value "9," which is provided by the control circuit 50, to the moisture detection antenna electromotive force (11+9=20) is equal to or greater than the threshold value "6," and outputs the comparison result to the control circuit 50.

In the state shown in FIG. 9B, the difference is greater than the threshold value, and the comparison circuit 47 outputs information indicating that the difference is greater than the threshold value to the control circuit 50 as the comparison result. In this case, the control circuit 50 determines that there is moisture nearby, and sends the comparison result to the reader/writer 12 (See Step S108 in FIG. 5). If the difference is equal to or greater than the threshold value, the control circuit 50 may obtain at least one of the difference ("10" in the example shown in FIG. 9B) and the digital value of the moisture detection antenna electromotive force corrected by the correction value from the comparison circuit 47, and may output the information indicating the amount of moisture to the reader/writer 12 based on the obtained value. For example, if the correlation between the reduction of electromotive force and the moisture amount is found in advance, the moisture amount may be obtained based on the difference between the communication antenna electromotive force and the moisture detection antenna electromotive force and the correlation, and the obtained moisture amount may be output to the reader/writer 12.

As described above, in the RF tag 10 of this embodiment, the numerical values of the communication antenna electromotive force and the moisture detection antenna electromotive force are used for detecting moisture, which makes it easier to set the threshold, add the correction value, and the like. As a result, the effects of the manufacturing variations described above can be mitigated, and the moisture detection accuracy can therefore be improved.

Embodiment 3

Generally, the electromotive force generated in the RF tag by a radio wave received from the reader/writer varies depending on the distance between the RF tag and the reader/writer. The longer the distance between the RF tag and the reader/writer is, the more attenuated the radio wave is, and thus the weaker the intensity is, which reduces the electromotive force generated in the RF tag. Therefore, in the RF tag 10 of this embodiment, moisture is detected taking into consideration the distance between the reader/writer 12 and the RF tag 10 (will be referred to as the "communication distance" below).

The configuration of the RFID system 1 of this embodiment is the same as that of the RFID system 1 of Embodiment 1 (see FIG. 1). The configuration of the RF tag 10 of this embodiment is the same as that of the RF tag 10 of Embodiment 1 (see FIG. 2). The configuration of the IC chip 20 of this embodiment, however, differs from that of the IC chip 20 of Embodiment 1 (see FIG. 3).

Figure 10:
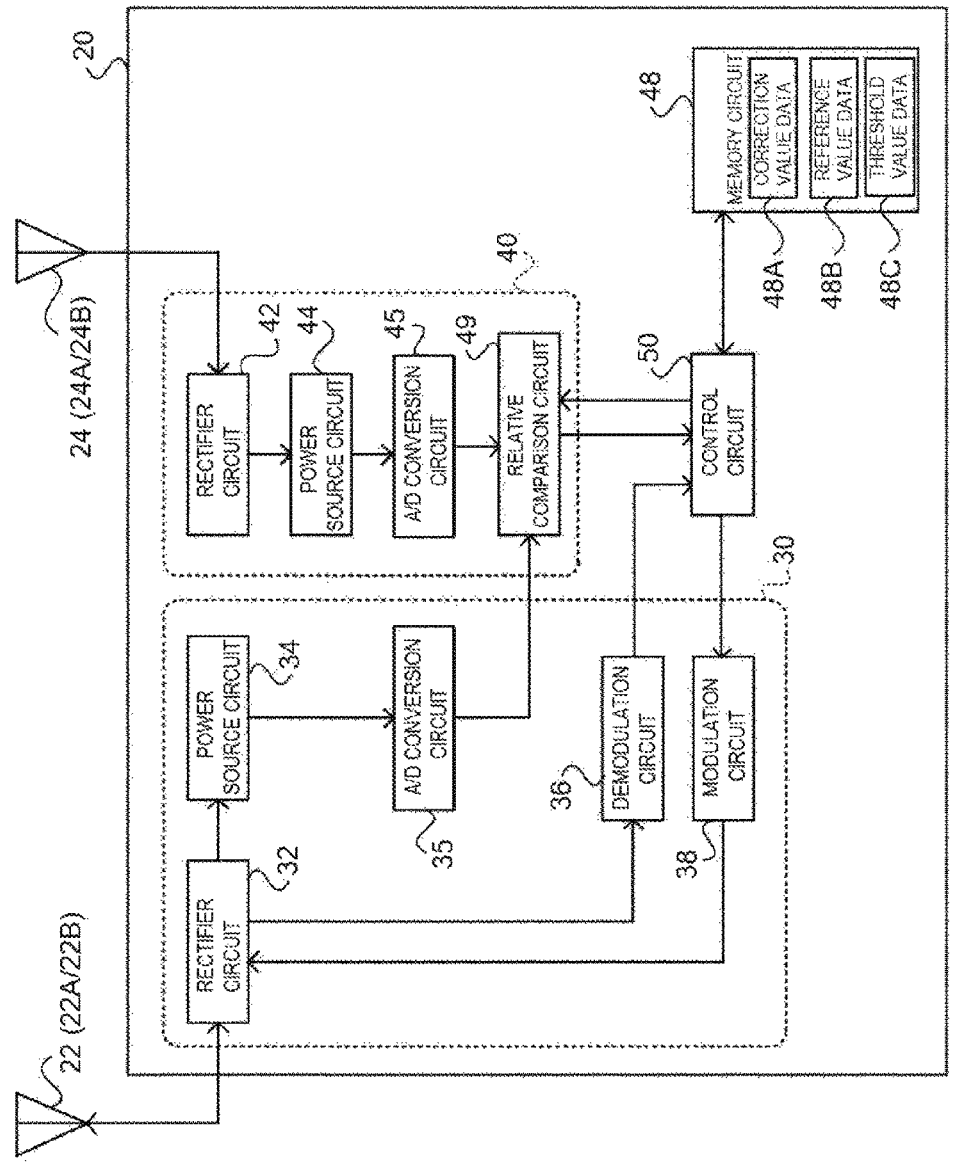
FIG. 10 is a block diagram showing the configuration of one example of an IC chip of Embodiment 2.

FIG. 10 is a block diagram showing the configuration of one example of an IC chip of this embodiment. As shown in FIG. 10, in a manner similar to the IC chip 20 of Embodiment 2 (see FIG. 7), the IC chip 20 of this embodiment differs from the IC chip 20 of Embodiment 1 (see FIG. 3) in that the RF control circuit 30 further includes an A/D (analog/digital) conversion circuit 35 and the sensor circuit 40 includes an A/D conversion circuit 45. Also, the IC chip 20 of this embodiment differs from the IC chip 20 of Embodiment 1 (see FIG. 3) in that the sensor circuit 40 includes a relative comparison circuit 49. Furthermore, as shown in FIG. 10, the IC chip 20 of this embodiment differs from the IC chip 20 of Embodiment 1 (see FIG. 3) in that the memory circuit 48 contains correction value data 48A, reference value data 48B, and threshold value data 48C. The correction value data 48A is the same as the correction value data 48A in the IC chip 20 of Embodiment 2 as described below in detail. The reference value data 48B represents a digital value of the communication antenna electromotive force when the correction value data 48A was obtained. The threshold value data 48C represents a threshold value similar to the threshold value used for detecting moisture in the IC chip 20 of Embodiment 2.

The relative comparison circuit 49 relatively compares a digital value provided by the A/D conversion circuit 35 with a digital value provided by the A/D conversion circuit 45 using the reference value, thereby correcting the change in electromotive force due to the communication distance.

Next, the operation of the IC chip 20 of this embodiment will be explained. The overall flow of the operation is similar to the operation of the IC chip 20 of Embodiment 1 (see FIG. 5), but the moisture detection operation of this embodiment differs from that of Embodiment 1, and therefore, the moisture detection operation in the IC chip 20 of this embodiment will be explained.

In Embodiment 2, the moisture detection antenna electromotive force was corrected using the correction value. However, as described above, depending on manufacturing variations of the IC chip 20, the communication antenna 22, and the moisture detection antenna 24 or the usage status of the RF tag 10 (such as the surrounding environment or attachment condition), the communication antenna electromotive force may differ from the moisture detection antenna electromotive force.

Figure 11A:
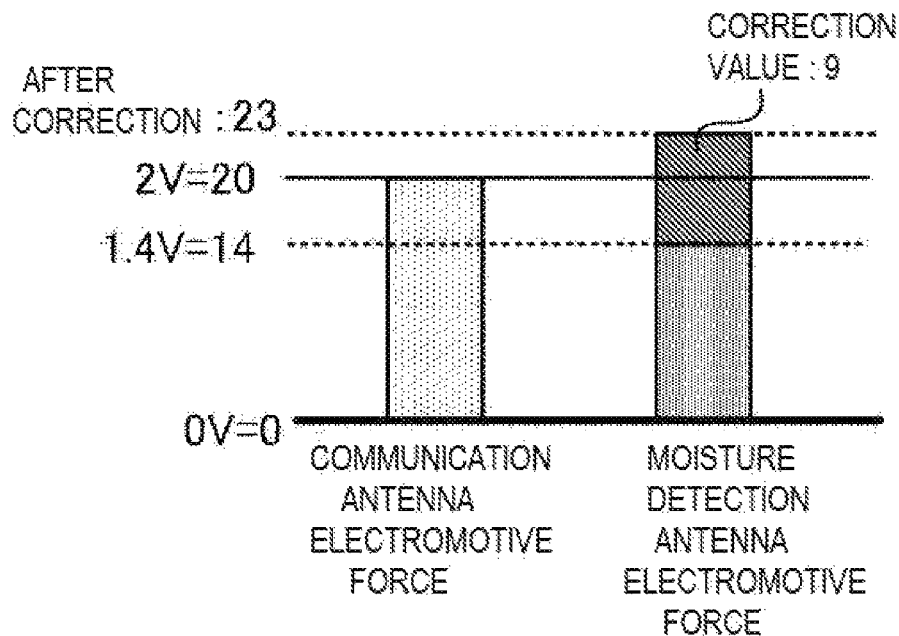
FIG. 11A is a diagram for explaining how to detect moisture by the RF tag when a correction value and a threshold value are not changed relative to each other.

Not in the RF tag 10 of this embodiment, but in the RF tag 10 of Embodiment 2, as shown in FIG. 11A, for example, if there was no moisture nearby and the communication distance was great (greater than the case shown in FIG. 8), the communication antenna electromotive force would be 2V (digital value is "20"), and the moisture detection antenna electromotive force would be 1.4V (digital value is "14"). In this case, if the correction value was "9," the communication antenna electromotive force varies from the moisture detection antenna electromotive force after correction even though there is no moisture nearby, and the moisture detection antenna electromotive force after correction is greater than the communication antenna electromotive force. Thus, in the case of FIG. 11A, the moisture detection accuracy would be lower.

Figure 11B:
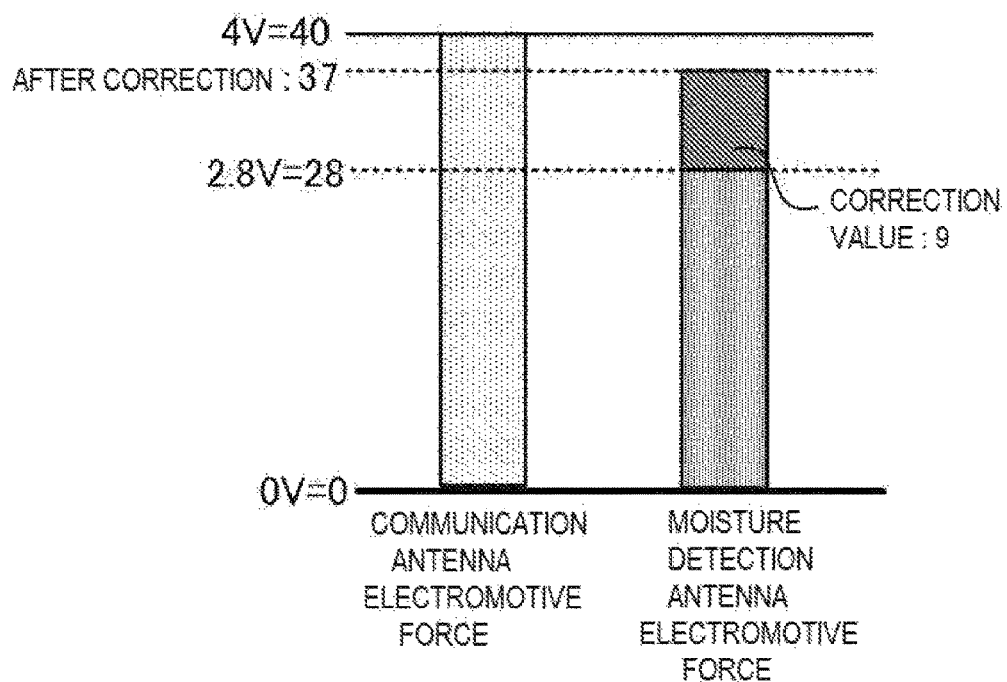
FIG. 11B is a diagram for explaining how to detect moisture by the RF tag when a correction value and a threshold value are not changed relative to each other.

Also, in the RF tag 10 of Embodiment 2, as shown in FIG. 11B, for example, if there was no moisture nearby and the communication distance was short (shorter than the case shown in FIG. 8), the communication antenna electromotive force would be 4V (digital value is "40"), and the moisture detection antenna electromotive force would be 2.8V (digital value is "28"). In this case, if the correction value was "9," the communication antenna electromotive force would vary from the moisture detection antenna electromotive force after correction even though there is no moisture nearby, and the moisture detection antenna electromotive force after correction would be smaller than the communication antenna electromotive force. Thus, in the case of FIG. 11B, the moisture detection accuracy would be lower.

On the contrary, in the IC chip 20 of this embodiment, the correction value is obtained, and a digital value of the communication antenna electromotive force when the correction value was obtained is also obtained as a reference value, and the correction value data 48A and the reference value data 48B are stored in the memory circuit 48 in advance, in a manner similar to the IC chip 20 of Embodiment 2. In the IC chip 20 of this embodiment, as described above, the threshold value data 48 indicating the threshold value used for moisture detection is also stored in the memory circuit 48 in advance.

Figure 12A:
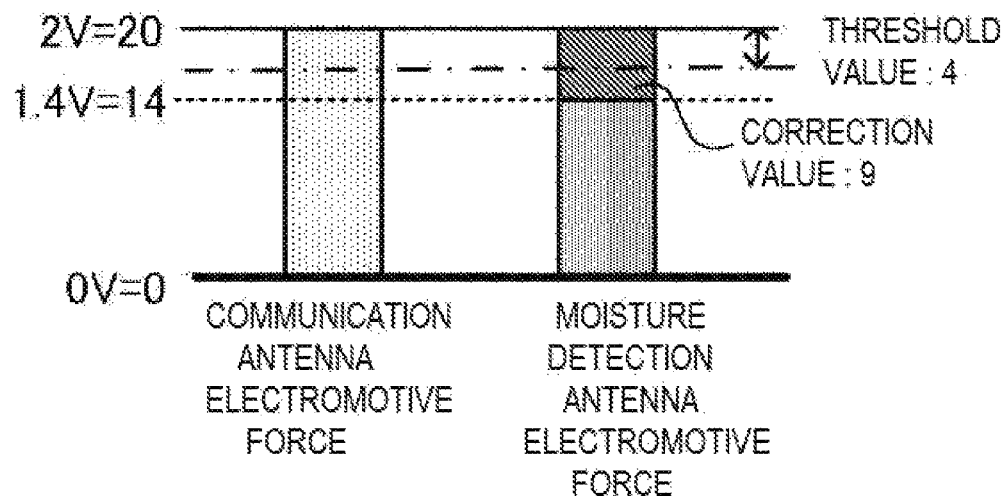
FIG. 12A is a diagram for explaining how to detect moisture by the RF tag of Embodiment 3.

For example, when the control circuit 50 of the IC chip 20 obtained the correction value, if the communication antenna electromotive force is "20" and the moisture detection antenna electromotive force is "14" as shown in FIG. 12A, the control circuit 50 obtains the difference, which is "6," and stores the value as the correction value data 48A in the memory circuit 48. The control circuit 50 also stores in the memory circuit 48 the communication antenna electromotive force, which is "20," as the reference value data 48B. Furthermore, in the case shown in FIG. 12A, the threshold value data 48C indicating "4," which is the threshold value, is stored in the memory circuit 48 in advance.

In this embodiment, when the relative comparison circuit 49 starts comparison, the control circuit 50 reads out the correction value data 48A, the reference value data 48B, and the threshold value data 48C from the memory circuit 48, and outputs each data to the relative comparison circuit 49.

Figure 12B:
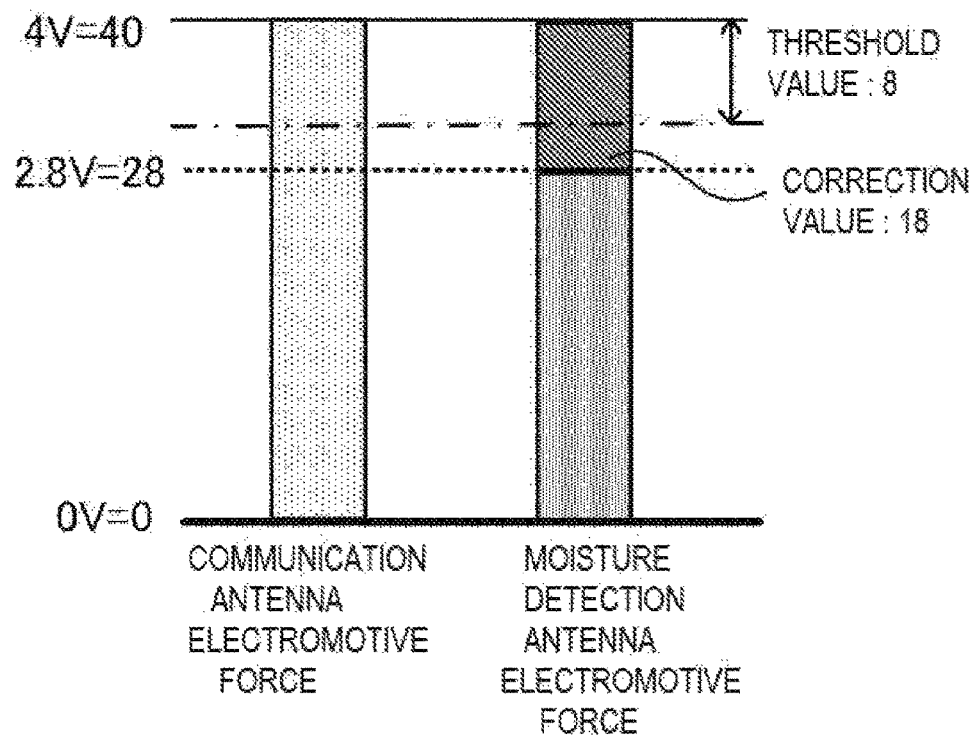
FIG. 12B is a diagram for explaining how to detect moisture by the RF tag of Embodiment 3.

If the moisture detection is conducted thereafter, as shown in FIG. 12B, for example, the shorter the communication distance, the greater the communication antenna electromotive force and the moisture detection antenna electromotive force. FIG. 12B shows a state where there is no moisture nearby.

In the case shown in FIG. 12B, the communication antenna electromotive force is "40," which is twice as much as the reference value of "20." Thus, the relative comparison circuit 49 uses "12" as the correction value, which is twofold the correction value "6" of the correction value data 48A, to correct the moisture detection antenna electromotive force. Therefore, in the case shown in FIG. 12B, the moisture detection antenna electromotive force after correction is "40" (28+12=40).

The relative comparison circuit 49 also determines whether the difference between the communication antenna electromotive force and the moisture detection antenna electromotive force is smaller than the threshold value or not, using "8" as the threshold value, which is double the threshold value "4" of the threshold value data 48C, and outputs the comparison result to the control circuit 50.

In the case shown in FIG. 12B, the communication antenna electromotive force and the moisture detection antenna electromotive force after correction are the same, which makes the difference between the two smaller than the threshold value, and thus, the control circuit 50 determines that there is no moisture nearby.

As described above, in the RF tag 10 of this embodiment, the correction value and the threshold value are relatively changed based on the electromotive forces corresponding to the communication distance, which makes it possible to improve the moisture detection accuracy.

The RF tag 10 of each of the embodiments described above includes: the moisture detection antenna 24 that receives a radio wave transmitted from the reader/writer 12 and that is used to detect moisture; the communication antenna 22 that receives a radio wave transmitted from the reader/writer 12 and that transmits a radio wave to the reader/writer 12; and the control circuit 50 that transmits to the reader/writer 12 via the communication antenna 22 a comparison result between the moisture detection antenna electromotive force generated by the radio wave received by the moisture detection antenna 24 and a communication antenna electromotive force generated by the radio wave received by the communication antenna 22.

As described above, the RF tag 10 of each of the embodiments described above includes two types of antennas: the communication antenna 22 and the moisture detection antenna 24. This way, the effect of moisture on the communication antenna 22 can be suppressed, which makes it possible to mitigate the degradation of the communication property.

In the RF tag 10 of each of the embodiments above, the presence or absence of moisture is detected based on the comparison result between the communication antenna electromotive force and the moisture detection antenna electromotive force, and therefore, as compared with the case of using the communication antenna only, the accuracy of moisture detection can be improved.

In the RF tag 10 of each of the embodiments described above, a power source voltage for operating each part of the IC chip 20 is obtained from the electromotive force generated by the radio wave received from the reader/writer 12. Thus, it is possible to suppress the power consumption, and it is possible to eliminate the necessity of installing a power source such as a battery. As a result, it is possible to reduce the size and price of the detection device as compared to other detection devices that require a power source to be installed therein.

In the RF tag 10 of each of the embodiments described above, it is possible to detect moisture that is not directly in contact with the RF tag 10. Therefore, the RF tag 10 is not contaminated by the moisture to be detected. This makes it possible to suppress the maintenance cost and manufacturing cost of the RF tag 10, for example.

Figure 14:
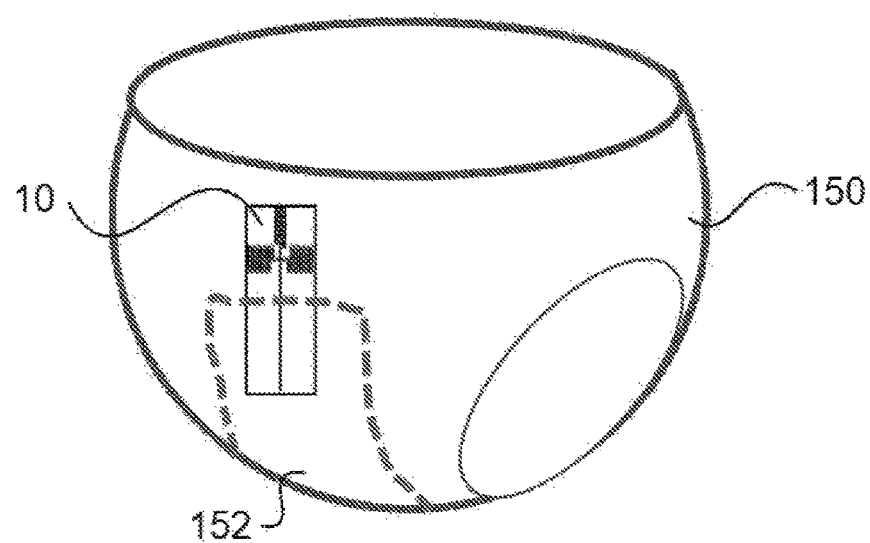
FIG. 14 is a diagram for explaining an example of the application of the RF tag of each embodiment.

There is no special limitation on the application of the RF tag 10 of each of the embodiments described above, and for example, the RF tag 10 may be applied to detect moisture in a disposable diaper 150 as shown in FIG. 14. In this case, as shown in FIG. 14, the RF tag 10 is pasted above water-absorbing polymer 152 of the disposable diaper 150 (further away from legs). Because the RF tag 10 can be pasted outside of the disposable diaper 150, it is possible to prevent the RF tag 10 from being contaminated by waste products. The RF tag 10 can be removed from the diaper 150 before disposition so it can be used again.

It is needless to say that the RF tag 10 can be pasted on a container 100 or a container 102 as shown in FIG. 6 to detect the presence or absence of moisture or to determine whether the moisture amount exceeds a prescribed amount or not.

When the RF tag 10 is completely in contact with moisture, the communication antenna electromotive force is equal to the moisture detection antenna electromotive force in a manner similar to the state where there is no moisture nearby. Thus, it is also possible to configure the RF tag 10 such that the state where the RF tag 10 is completely in contact with moisture is an initial state, and by detecting a change in the moisture detection antenna electromotive force from the state where the communication antenna electromotive force is equal to the moisture detection antenna electromotive force, the control circuit 50 determines that the RF tag 10 is no longer in contact with moisture or that the amount of moisture in contact with the RF tag 10 has reduced.

Figure 13A:
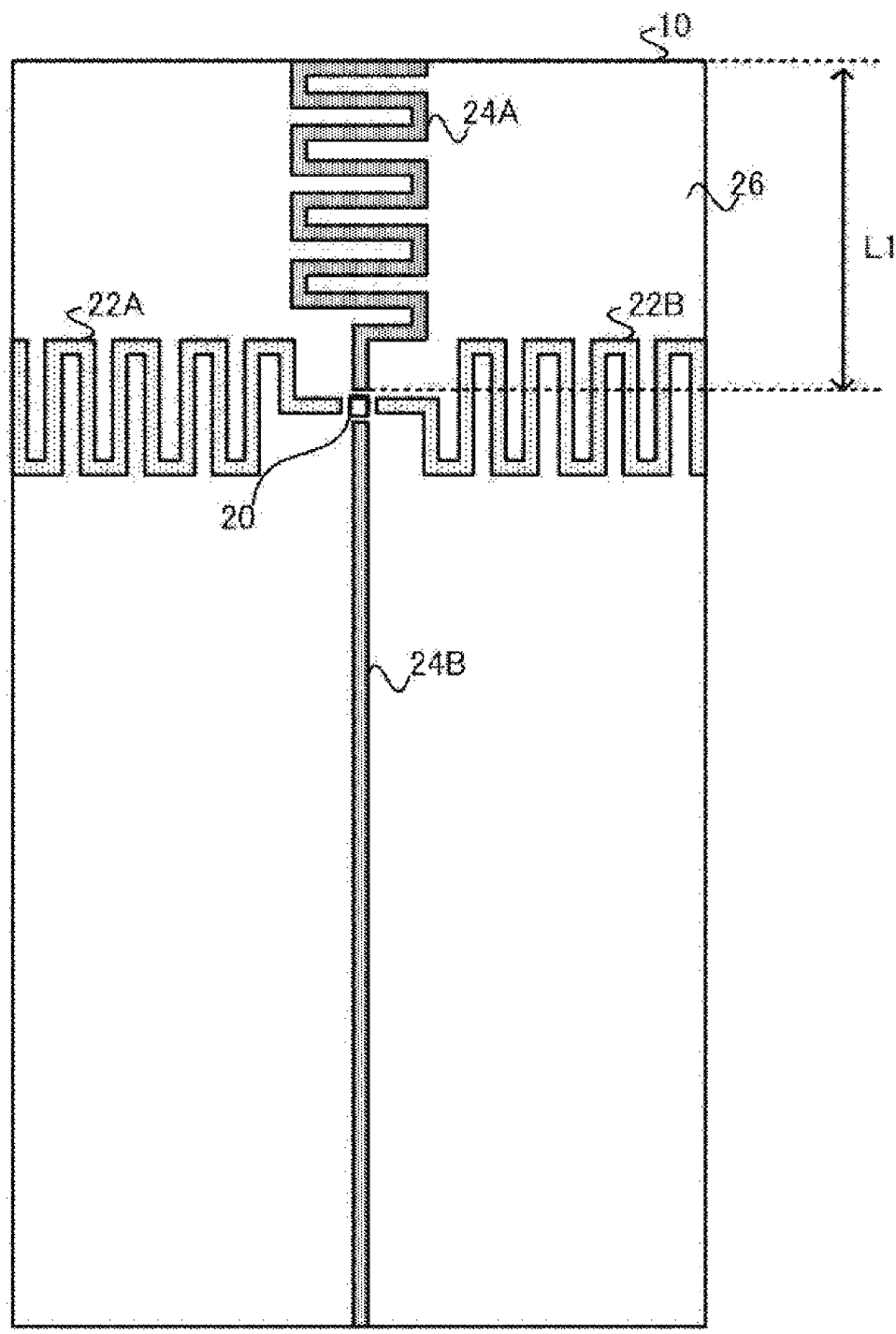
FIG. 13A is a plan view of the RF tag, showing another example of the moisture detection antenna.

The shape of the communication antenna 22 and the moisture detection antenna 24 is not limited to that shown in each embodiment (see FIG. 2). For example, as shown in FIG. 13A, the antenna element 24B of the moisture detection antenna 24 may be arranged as a straight line. In this case, because the length of the antenna element 24B in the wiring direction is greater, it is possible to detect the presence of moisture near the RF tag 10 sooner. For example, in the case of FIG. 6, by pasting the RF tag 10 shown in FIG. 13 on the outer surface of the container 100 or container 102, it is possible to detect the approaching surface of the liquid 110 sooner than the RF tag 10 of each embodiment described above. In the example shown in FIG. 13A, a sufficient distance can be ensured between the communication antenna 22 (antenna element 22A and antenna element 22B) and moisture to be detected, which suppresses the effect of the moisture on the communication antenna 22, and as a result, the communication property can be made more stable. This makes it possible to increase the communication distance, for example.

Figure 13B:
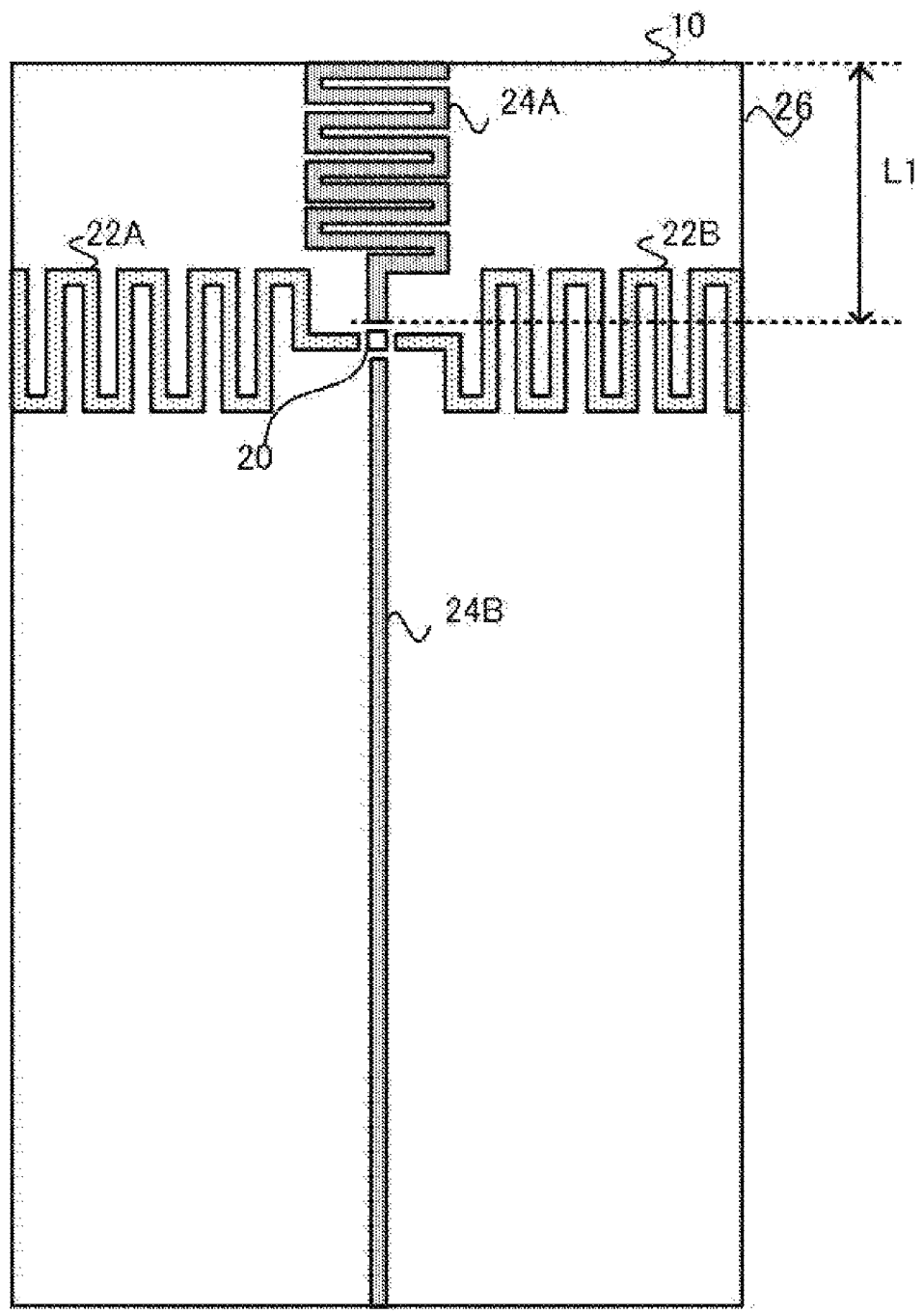
FIG. 13B is a plan view of the RF tag, showing another example of the moisture detection antenna.

Furthermore, as shown in FIG. 13B, for example, the length L1 in the wiring direction of the area where the antenna element 24B of the moisture detection antenna 24 is arranged may be shorter than the length (see L1 of FIG. 13) in the wiring direction of the area where the antenna element 24B is arranged in each embodiment above or in the RF tag 10 of FIG. 13A. By making the length L1 shorter, it is possible to reduce the size of the RF tag 10. In this case, taking into account the effect on the moisture detection antenna electromotive force, it is preferable that the moisture detection antenna be a negative antenna of the pair of negative and positive antennas.

There is no special limitation on the shape, arrangement, and wiring pattern of the communication antenna 22 and the moisture detection antenna 24, considering the effects thereof on the communication and electromotive force. For example, the antenna elements 22A and 22B, and the antenna elements 24A and 24B may be folded in a different manner from that of each embodiment described above. The antenna elements 22A and 22B and the antenna element 24A and 24B may also be curved or formed in an arch shape, for example.

As shown in each embodiment described above, or in FIGS. 13A and 13B, by arranging the communication antenna 22 and the moisture detection antenna 24 such that the respective wiring directions intersect with each other, i.e., the cross structure, a sufficient distance can be ensured between the communication antenna 22 and the moisture to be detected, which suppresses the effect of moisture on the communication, and as a result, the degradation of the communication property can be avoided.

In Embodiment 2 and Embodiment 3, the RF control circuit 30 includes the A/D conversion circuit 35, and the sensor circuit 40 includes the A/D conversion circuit 45, but the invention is not limited to such a configuration. For example, a common circuit may be used for the A/D conversion circuit 35 and the A/D conversion circuit 45. In this case, the conversion of the communication antenna electromotive force and the conversion of the moisture detection antenna electromotive force are conducted in series, which would increase the processing time, but the size of the IC chip 20 can be reduced.

Other configurations, operation, and the like of the RFID system 1, the RF tag 10, and the IC chip 20 described in each embodiment above are mere examples, and it is needless to say that those may be modified without departing from the scope of the invention.

What is claimed is:

1. A detection device for detecting existence of moisture, comprising:
   a first antenna configured to receive a first radio wave transmitted from an external device;
   a second antenna configured to
      receive the first radio wave transmitted from the external device, and
      transmit a second radio wave to the external device; and
   a chip configured to
      obtain a comparison result between a first electromotive force generated by the first radio wave received by the first antenna and a second electromotive force generated by the first radio wave received by the second antenna, and
      to send the comparison result to the external device through the second radio wave, such that
   when the first antenna is disposed closer than the second antenna to a place where the existence of moisture is to be detected, a change of the first electromotive force is greater than a change of the second electromotive force in response to the existence of moisture; wherein
   the first antenna is disposed in a first wiring direction and the second antenna is disposed in a second wiring direction that intersects the first wiring direction, and
   the first wiring direction intersects the second wiring direction at a position corresponding to a position where the chip is disposed.

2. The detection device according to claim 1, wherein
   the first antenna includes a first antenna element and a second antenna element that are disposed to face each other across the chip, and
   the second antenna includes a third antenna element and a fourth antenna element that are disposed to face each other across the chip.

3. The detection device according to claim 2, wherein at least one of the first antenna element and the second antenna element includes a bend or a curve.

4. The detection device according to claim 2, wherein
   the first antenna element, the chip, and the second antenna element are arranged along a predetermined direction, and
   a length of an area where the first antenna element is disposed in the predetermined direction differs from a length of an area where the second antenna element is disposed in the predetermined direction.

5. The detection device according to claim 2, wherein
   the first antenna element, the chip, and the second antenna element are arranged along a predetermined direction that is parallel to the first wiring direction, and
   a length of an area where the first antenna element is disposed in the predetermined direction differs from a length of an area where the second antenna element is disposed in the predetermined direction.

6. The detection device according to claim 1, wherein the detection device is a radio frequency (RF) tag for a radio frequency identifier (RFID).

7. A method of using a detection device for detecting existence of moisture, the detection device including a first antenna configured to receive a first radio wave transmitted from an external device, and a second antenna configured to receive the first radio wave transmitted from the external device, and transmit a second radio wave to the external device, and a chip configured to obtain a comparison result between a first electromotive force generated by the first radio wave received by the first antenna and a second electromotive force generated by the first radio wave received by the second antenna, and to send the comparison result to the external device through the second radio wave, the method comprising:
  disposing the first antenna in a first wiring direction and disposing the second antenna in a second wiring direction that intersects the first wiring direction, the first wiring direction intersecting the second wiring direction at a position corresponding to a position where the chip is disposed;
  disposing the first antenna closer than the second antenna to a place where the existence of moisture is to be detected; and
  in response to a change of the first electromotive force that is varied greater than a change of the second electromotive force, detecting the existence of moisture.

* * * * *